(12) United States Patent
Konakanchi et al.

(10) Patent No.: US 11,111,228 B2
(45) Date of Patent: Sep. 7, 2021

(54) PROCESS FOR THE PREPARATION OF POMALIDOMIDE AND ITS PURIFICATION

(71) Applicant: Natco Pharma Limited, Hyderabad (IN)

(72) Inventors: Durga Prasad Konakanchi, Hyderabad (IN); Buchappa Gongalla, Hyderabad (IN); Dharmendher Ragidi, Hyderabad (IN); Uma Naresh Babu Kotra, Hyderabad (IN); Kali Satya Bhujanga Rao Adibhatla, Hyderabad (IN); Venkaiah Chowdary Nannapaneni, Hyderabad (IN)

(73) Assignee: Natco Pharma Limited, Hyderabad (IN)

( * ) Notice: Subject to any disclaimer, the term of this patent is extended or adjusted under 35 U.S.C. 154(b) by 0 days.

(21) Appl. No.: 16/311,782

(22) PCT Filed: Aug. 22, 2016

(86) PCT No.: PCT/IN2016/050278
§ 371 (c)(1),
(2) Date: Dec. 20, 2018

(87) PCT Pub. No.: WO2017/221261
PCT Pub. Date: Dec. 28, 2017

(65) Prior Publication Data
US 2019/0233389 A1     Aug. 1, 2019

(30) Foreign Application Priority Data
Jun. 23, 2016 (IN) .............................. 201641021533

(51) Int. Cl.
*C07D 401/04*     (2006.01)
(52) U.S. Cl.
CPC .................................. *C07D 401/04* (2013.01)
(58) Field of Classification Search
CPC .................................................. C07D 401/04
See application file for complete search history.

(56) References Cited

U.S. PATENT DOCUMENTS

| | | | | |
|---|---|---|---|---|
| 3,423,462 A | * | 1/1969 | Rylander | ............... C07C 209/36 564/423 |
| 3,855,185 A | * | 12/1974 | Loveless | ................. C08C 19/02 525/338 |
| 5,093,535 A | * | 3/1992 | Harrison | ............... C07C 29/141 568/881 |
| 5,635,517 A | | 6/1997 | Muller et al. | |

FOREIGN PATENT DOCUMENTS

| | | | |
|---|---|---|---|
| CN | 103626735 A | | 3/2014 |
| CN | 104016967 A | * | 9/2014 |
| CN | 104387366 A | * | 3/2015 |
| CN | 104402863 A | * | 3/2015 |
| CN | 104402863 A | | 3/2015 |
| WO | WO/2013/126326 A1 | | 8/2013 |

OTHER PUBLICATIONS

Varala "Practical and Efficient Synthesis of Thalidomide via Na/Liquid NH3 Methodology1" Organic Process Research & Development 2005, 9, 853-856.*
Database WPI, "AN 2015-26815U XP002767754, -& CN 104 402 863 A (Hangzhou Simbos Pharm co Ltd) Mar. 11, 2015 (Mar. 11, 2015) abstract", Thomson Scientific, London, GB, Week 201550.
Database WPI, "XP002767755, -& CN 103 626 738 A (Chongqing Taihao Pharm Co Ltd) Mar. 12, 2014 (Mar. 12, 2014) abstract; claims 3-5; examples 1-4", Thomson Scientific, London, GB, Week 201461.
Huang, Daowei et al., "A New Synthesis Route for the Preparation of Pomalidomide", Synthetic Communications, vol. 46, No. 16, May 24, 2016.
Hanna, et al., "The Absorption Spectra of Derivatives of Phthalic Anhydride", Proceedings of the Iowa Academy of Science, vol. 58, No. 1, 1951, 251-260.
Kayser, et al., "On the Mechanism of Wittig Reactions With Cyclic Anhydrides. li", Canadian Journal of Chemistry, vol. 71, No. 7, Jul. 1993, 1010-1021.
Vogel, A Text-Book of Practical Organic Chemistry, 1956, 422-425,654-655.

* cited by examiner

*Primary Examiner* — David K O'Dell
(74) *Attorney, Agent, or Firm* — Vos-IP, LLC

(57) ABSTRACT

The present invention is related to an improved process for the preparation of Pomalidomide with higher yields and high purity. Particularly the present invention relates to form A preparation of Pomalidomide and its purification. wherein the present process doesn't involve use of dioxane solvent and avoids higher temperatures.

4 Claims, 3 Drawing Sheets

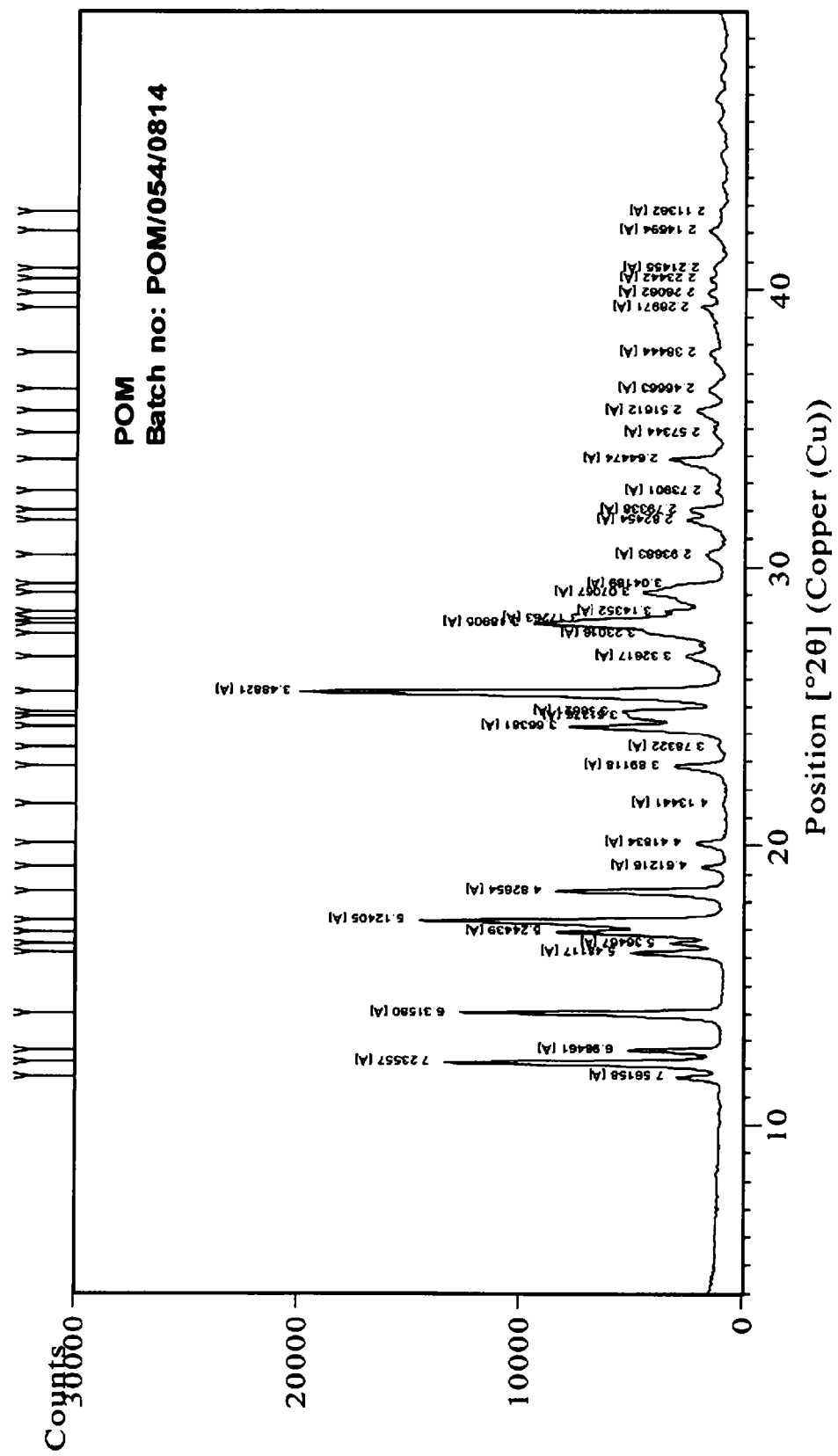
Fig. 1 Powder X-ray diffractogram of Form A of Pomalidomide

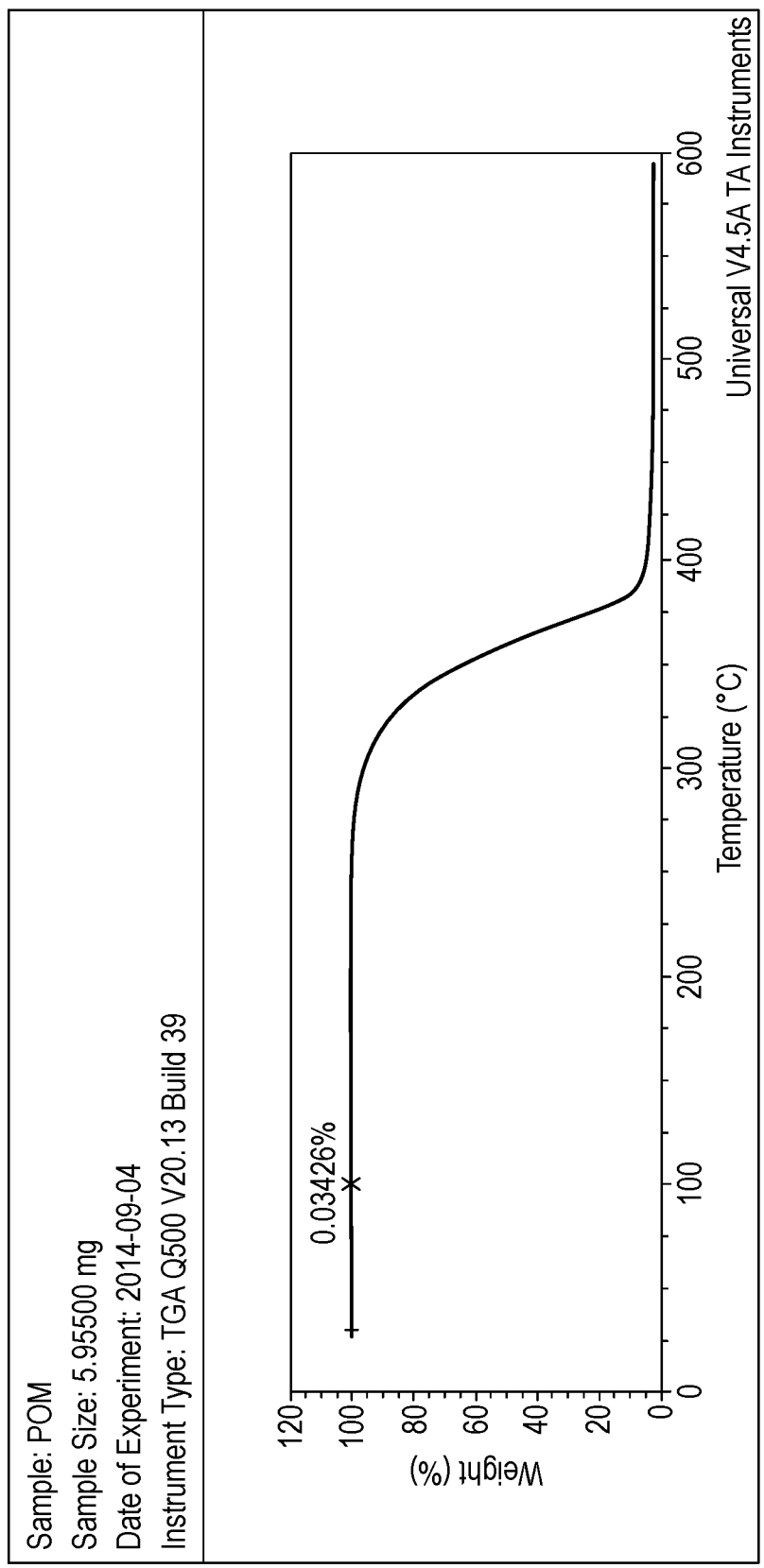
Fig. 2   TGA of Form A of Pomalidomide

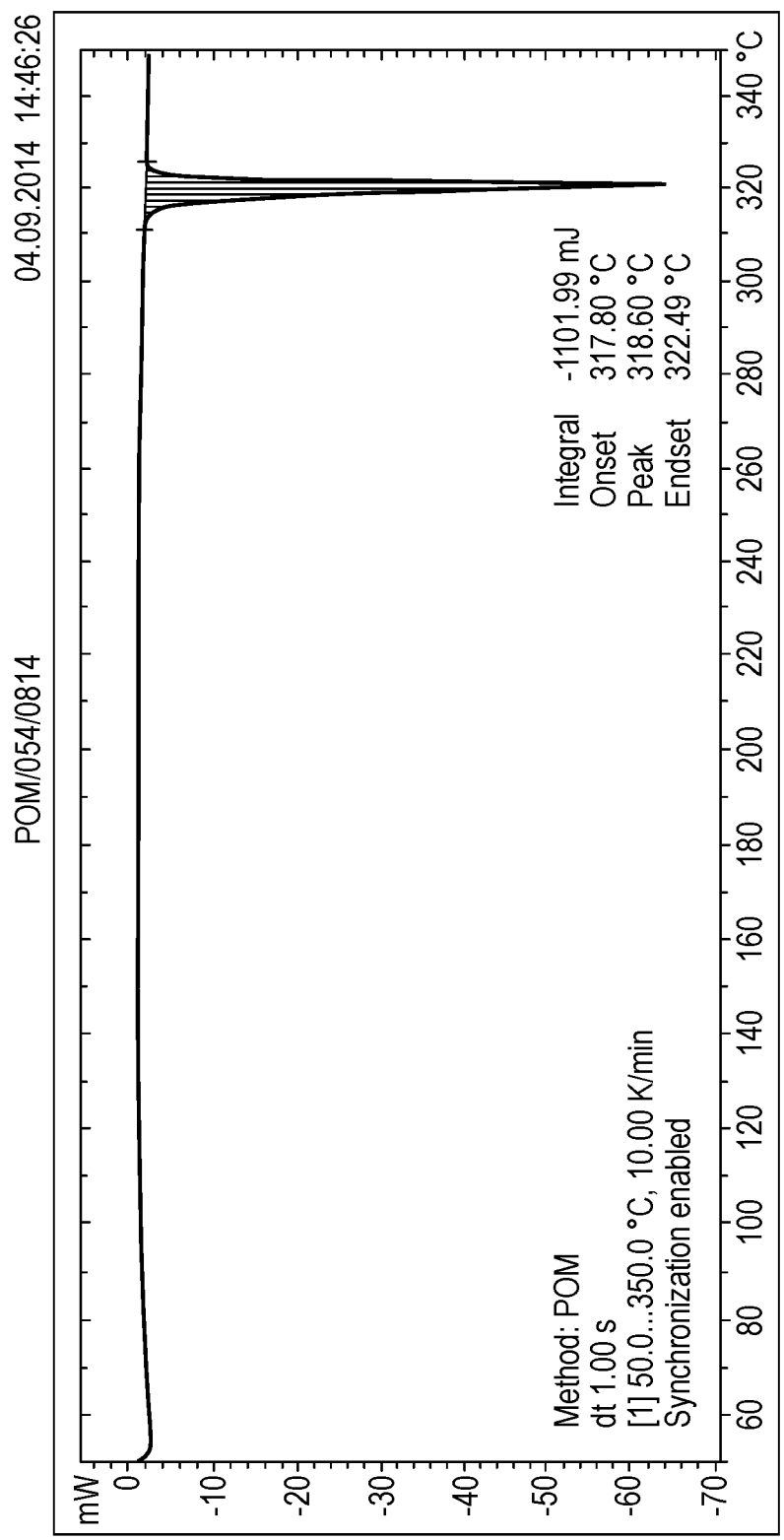
Fig. 3    DSC of Form A of Pomalidomide

PROCESS FOR THE PREPARATION OF POMALIDOMIDE AND ITS PURIFICATION

FIELD OF THE INVENTION

The present invention is related to an improved process for the preparation of Pomalidomide with higher yields and high purity. Particularly the present invention relates to form A preparation of Pomalidomide and its purification.

BACKGROUND OF THE INVENTION

Pomalidomide is chemically known as (RS)-4-amino-2-(2, 6-dioxo-piperidin-3-yl)-isoindoline-1, 3-dione and structurally represented as below:

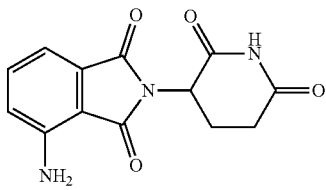 [SMILES: Nc1cccc2c1C(=O)N(C1CCC(=O)NC1=O)C2=O]

Pomalidomide is an immunomodulatory-antineoplastic agent. Pomalidomide is marketed with the brand name POMALYST®. It is indicated for the treatment of relapsed and refractor multiple myeloma.

Pomalidomide and its process were disclosed in U.S. Pat. No. 5,635,517. wherein, crystalline solid of pomalidomide was obtained by reacting of 3-nitrophthalic anhydride with, 3-aminoglutarimide hydrochloride in presence of sodium acetate and acetic acid to get 1, 3-dioxo-2(2, 6-dioxopiperidin-3-yl)-5-nitroisoindoline and reducing the 1, 3-dioxo-2(2, 6-dioxopiperidin-3-yl)-5-nitroisoindoline with palladium carbon in the presence of 1, 4-dioxane, filtered and then concentrated to obtain a residual solid. The residual solid was recrystallized with 1, 4-dioxane and ethyl acetate to obtain crystalline pomalidomide.

PCT application no. WO2013126326A2 has disclosed the form A of pomalidomide, wherein the form A has prepared by dissolving pomalidomide in a solvent (Acetonitrile, methyl ethyl ketone, tetrahydrofuran) at 80° C. and cooled to obtain form A. This application also discloses solvent/anti-solvent (tetrahydrofuran/heptane) process in the ration of 1:3 to obtain form A.

The inventors of the present of invention have developed an improved process for the preparation of form A of pomalidomide with high yield and purity. The present process is cost effective and feasible in large scale production also.

SUMMARY OF THE INVENTION

One aspect of the present invention is to provide a process for the preparation of pomalidomide form A comprising the steps of:
a) reacting 3-nitrophthalic acid with acetic anhydride in presence of toluene to get 3-nitrophthalic anhydride,
b) reacting 3-nitrophthalic anhydride with 3-aminoglutarimide hydrochloride in presence of tri ethylamine and acetic acid solvent to get 2-(2, 6-dioxo-3-piperidyl)-4-nitro-isoindoline-1, 3-dione,
c) reducing the 2-(2, 6-dioxo-3-piperidyl)-4-nitro-isoindoline-1, 3-dione in presence of Pd/C and dimethyl formamide solvent to get pomalidomide form A.

Another aspect of the present invention is to provide a process for the purification of pomalidomide form A comprising the steps of:
a) dissolving the pomalidomide form A in dimethyl sulfoxide,
b) stirring the reaction mixture obtained in step a) at room temperature,
c) adding the reaction mass obtained in step b) to water,
d) stirring the reaction mass obtained in step c) at room temperature and
e) isolating pure pomalidomide form A.

DETAILED DESCRIPTION OF THE INVENTION

The present invention relates to an improved process for the preparation of pomalidomide, wherein the present process doesn't involve use of dioxane solvent and avoids higher temperatures.

One embodiment of the present invention is to provide a process for the preparation of pomalidomide form A comprising the steps of:
a) reacting 3-nitrophthalic acid with acetic anhydride in presence of toluene to get 3-nitrophthalic anhydride,
b) reacting 3-nitrophthalic anhydride with 3-aminoglutarimide hydrochloride in presence of tri ethylamine and acetic acid solvent to get 2-(2, 6-dioxo-3-piperidyl)-4-nitro-isoindoline-1, 3-dione,
c) reducing the 2-(2, 6-dioxo-3-piperidyl)-4-nitro-isoindoline-1, 3-dione in presence of Pd/C and dimethyl formamide solvent to get pomalidomide form A.

According to the present invention, 3-nitrophthalic acid and acetic anhydride, toluene are added and is stirred for 5-10 min at 25-35° C. Reaction mass temperature is raised to reflux and maintained for 20-30 min. Reaction mass is cooled to 25-35° C., Solid reaction mass is filtered under vacuum, washing is given with toluene, suck dried for 10-15 min and obtained the 3-nitrophthalic anhydride.

In to a well cleaned RB flask, 3-aminoglutarimide hydrochloride and acetic acid are charged and stirred for 5-10 min at 25-35° C. 3-nitrophthalic anhydride is charged in to the reaction mass. and stirred for 5-10 min at 25-35° C., triethyl amine is added to the reaction mass, at 25-35° C., in about 30-45 min and maintained at same temperature for 20-30 min. Reaction mass temperature is raised to reflux and maintained for 3.0-3.5 hours and reaction mass is cooled to 25-35° C., maintained for 45-60 min. Solid reaction mass is filtered under vacuum, washing is given with DM Water, suck dried for 20-30 min to get 2-(2, 6-dioxo-3-piperidyl)-4-nitro-isoindoline-1, 3-dione.

In to a well cleaned and RB flask 2-(2, 6-dioxo-3-piperidyl)-4-nitro-isoindoline-1, 3-dione, dimethylformamide are charged. Reaction mass is stirred for 10-15 min at 25-35° C., clear solution is observed. 10% Pd/c is charged in to the reaction mass, in presence of N2 gas atmosphere, washing is given with dimethylformamide. H2 gas is bubbled in to the reaction mass, for 6.5-7.0 hours, at 15-20° C. after completion of the reaction, reaction mass is filtered under vacuum, through hyflow, in presence of N2 gas atmosphere, washing is given with dimethylformamide. Filtrate is transferred in to a 5.0 L 4 neck RB flask. Slowly added DM Water to the reaction mass over a period of 45-60 min at 15-20° C., Stirred the reaction mass at 15-20° C. for 60-90 min. Solid reaction mass is filtered under vacuum, washing is given with Water and isolated pomalidomide form A.

Another embodiment of the present invention is to provide a process for the purification pomalidomide form A comprising the steps of:
a) dissolving the pomalidomide in dimethyl sulfoxide,
b) stirring the reaction mixture obtained in step a) at room temperature,
c) adding the reaction mass obtained in step b) to water,
d) stirring the reaction mass obtained in step c) at room temperature and
e) isolating pure pomalidomide form A.

According to the present invention, Into a RB flask, pomalidomide form A, di methyl sulfoxide are charged. Reaction mass is stirred for 10-15 min at 25-35° C., clear solution is formed. Charged activated carbon into the reaction mass. Maintained for 30-45 min, at 25-35° C. Reaction mass is filtered through Buchner funnel under vacuum. Washed the carbon bed with di methyl sulfoxide. Charged water into a RB flask and cooled to 25-35° C. Added the reaction mass slowly to DM Water, at 25-35° C. in about 45-60 min. Solid formation is observed. Maintained the solid mass, at 25-35° C., for 60-90 min. Solid mass is filtered under vacuum, washing is given with Water, suck dried for 60-90 min. Wet compound is unloaded and dried. The obtained pomalidomide is form A of pomalidomide.

Yet another embodiment of the present invention relates to a pomalidomide form A with particle size d90 less than 10 microns, d50 less than 2 microns and d10 less than 1 micron.

Advantages of the present process:
Present process doesn't involve use of dioxane solvent and avoids higher temperatures.
In each stage of reaction yield were improved compared to prior art process.
API dissolution property also increased by decreasing the particle size to less than 5 microns.

The following examples are provided for illustration purpose only and are not intended to limit the scope of invention.

BRIEF DESCRIPTION OF DRAWINGS

FIG. 1: Powder X-ray diffractogram of Form A of Pomalidomide
FIG. 2: TGA of Form A of Pomalidomide
FIG. 3: DSC of Form A of Pomalidomide

EXPERIMENTAL SECTION

Example-1: Preparation of 3-nitrophthalic Anhydride

In to a well cleaned and 1.0 L 4 neck RB flask, 100.0 g of 3-nitrophthalic acid and 60.36 g of acetic anhydride, 500.0 ml of toluene were charged. Reaction mass was stirred for 5-10 min at 25-35° C. Reaction mass temperature was raised to reflux and maintained for 20-30 min. after completion of reaction, reaction mass was cooled to 25-35° C., Reaction mass was stirred for 60-90 min at 25-35° C. Solid reaction mass was filtered under vacuum, washing was given with 40.0 ml of toluene, suck dried for 10-15 min. Wet compound was unloaded. Wet compound is dried in a vacuum oven, at 60-65° C., for 3.0-4.0 hours, under vacuum (600-650 mm/Hg). Dried sample is transferred into a clean and dry polythene bag under nitrogen.

Yield: 74.0 g.

Example-2: Preparation of 2-(2, 6-dioxo-3-piperidyl)-4-nitro-isoindoline-1, 3-dione In to a well cleaned and oven dried 2.0 L 4 neck RB flask, 97.96 g of 3-aminoglutarimide hydrochloride and 500.0 ml of Acetic acid were charged. Reaction mass was stirred for 5-10 min at 25-35° C. 100.0 g of 3-nitrophthalic anhydride was charged in to the reaction mass. Reaction mass was stirred for 5-10 min at 25-35° C. 114.8 g of Triethyl amine was added to the reaction mass, at 25-35° C., in about 30-45 min. Reaction mass was maintained at 25-35° C., for 20-30 min. Reaction mass temperature was raised to reflux, maintained for 3.0-3.5 hours. After completion reaction, reaction mass was cooled to 25-35° C., maintained for 45-60 min. Solid reaction mass was filtered under vacuum, washing was given with 200.0 ml of DM water, suck dried for 20-30 min. Wet compound is charged in to the 500.0 ml 4 neck RB flask, 460.0 ml of DM water was charged in to the flask. Reaction mass was stirred for 20-30 min, at 25-35° C. Solid reaction mass was filtered under vacuum, washing was given with 200.0 ml of DM Water, suck dried for 45-60 min. Wet compound was dried in a vacuum oven, at 60-65° C., for 3-4 hours, under vacuum. (680 mm/Hg).

Yield: 141.6.0 g

Example-3: Preparation of Pomalidomide Form A

In to a well cleaned and oven dried 3.0 L 4 neck RB flask, to a mechanical stirrer and equipped with thermometer socket, condenser (fitted with gas outlet dipped in to the water), gas-inlet (connected with single trap filled with dimethylformamide up to bubbling nozzle), 100.0 g of 2-(2, 6-dioxo-3-piperidyl)-4-nitro-isoindoline-1, 3-dione, 1550.0 ml of dimethylformamide were charged. Reaction mass was stirred for 10-15 min at 25-35° C., clear solution was observed.

13.0 g of 10% Pd/c was charged in to the reaction mass, in presence of N2 gas atmosphere, washing was given with 50.0 ml of dimethylformamide. H2 gas was bubbled in to the reaction mass, for 6.5-7.0 hours, at 15-20° C. After completion of reaction, reaction mass is filtered under vacuum, through hyflow, in presence of N2 gas atmosphere, washing is given with 300.0 ml of dimethylformamide. Filtrate is transferred in to a 5.0 L 4 neck RB flask. Slowly added DM Water (1900.0 ml) to the reaction mass over a period of 45-60 min at 15-20° C., Stirred the reaction mass at 15-20° C. for 60-90 min. Solid reaction mass was filtered under vacuum, washing was given with 200.0 ml DM Water, suck dried for 45-60 min. wet compound is dried in a vacuum oven at 60-650 C, under vacuum (600-650 mm/Hg) for 2-3 hours and characterized as form A of pomalidomide.

Yield: 85.0 g

Example-4: Purification of Pomalidomide Form A

In to a well cleaned and dried 2.0 L 4-neck RB flask, 100.0 g of pomalidomide form A, 1000.0 ml of, di methyl sulfoxide are charged. Reaction mass was stirred for 10-15 min at 25-35° C., clear solution was formed. Charged 25.0 g of activated carbon into the reaction mass. Maintained for 30-45 min, at 25-35° C. Reaction mass was filtered through Buchner funnel under plant vacuum. Washed the carbon bed with 200.0 ml of di methyl sulfoxide. Charged DM Water (2000.0 ml) into a 5.0 L 4-neck RB flask and cooled to 25-35° C. Added the reaction mass slowly to DM Water, at 25-35° C. in about 45-60 min. Solid formation was observed. Maintained the solid mass, at 25-35° C., for 60-90 min. Solid mass is filtered under vacuum, washing was given with 200.0 ml DM Water, suck dried for 60-90 min. Wet compound is dried in a vacuum oven, at 60-650 C, for 35-36 hours, under vacuum (650-700 mm/Hg) and obtained as pure pomalidomide form A.

Yield: 90.0 g

What is claimed is:

1. A process for the preparation of pomalidomide form A comprising the steps of:
   a) reacting 3-nitrophthalic acid with acetic anhydride in presence of toluene to get 3-nitrophthalic anhydride,
   b) reacting 3-nitrophthalic anhydride with 3-aminoglutarimide hydrochloride in presence of tri ethylamine and acetic acid solvent to get 2-(2, 6-dioxo-3-piperidyl)-4-nitro-isoindoline-1, 3-dione,
   c) reducing the 2-(2, 6-dioxo-3-piperidyl)-4-nitro-isoindoline-1, 3-dione in the presence of Pd/C, dimethyl formamide solvent, and nitrogen, with hydrogen gas bubbled into the reaction mass, at 15° C. to 20° C. to get pomalidomide form A.

2. A process according to claim 1, wherein the mole ratio of 3-nitrophthalic acid with acetic anhydride is 1:1.8 moles.

3. A process according to claim 1 wherein the process further comprises steps for the purification of pomalidomide form A, comprising the steps of:
   d) dissolving the pomalidomide form A obtained in step c) in dimethyl sulfoxide,
   e) stirring the reaction mixture obtained in step d) at room temperature,
   f) adding the reaction mass obtained in step e) to water,
   g) stirring the reaction mass obtained in step f) at room temperature, and
   h) isolating pure pomalidomide form A.

4. A process according to claim 2 wherein the process further comprises steps for the purification of pomalidomide form A, comprising the steps of:
   d) dissolving the pomalidomide form A obtained in step c) in dimethyl sulfoxide,
   e) stirring the reaction mixture obtained in step d) at room temperature,
   f) adding the reaction mass obtained in step e) to water,
   g) stirring the reaction mass obtained in step f) at room temperature, and
   h) isolating pure pomalidomide form A.

* * * * *